(12) United States Patent
Hammond et al.

(10) Patent No.: US 7,601,000 B1
(45) Date of Patent: Oct. 13, 2009

(54) FACIAL PLANE INDICATOR

(75) Inventors: Daniel L. Hammond, Rockford, MI (US); Derek M. Draft, Zeeland, MI (US); Stuart D. Bowman, Rockford, MI (US)

(73) Assignee: Incisal Edge Products LLC, Grandville, MI (US)

( * ) Notice: Subject to any disclaimer, the term of this patent is extended or adjusted under 35 U.S.C. 154(b) by 0 days.

(21) Appl. No.: 11/276,420

(22) Filed: Feb. 28, 2006

Related U.S. Application Data

(60) Provisional application No. 60/597,197, filed on Nov. 16, 2005.

(51) Int. Cl.
*A61C 19/04* (2006.01)
(52) U.S. Cl. ........................................................ 433/68
(58) Field of Classification Search ................. 433/68, 433/69, 72, 73, 44, 55, 56, 33; 33/513, 514
See application file for complete search history.

(56) References Cited

U.S. PATENT DOCUMENTS

| | | | | |
|---|---|---|---|---|
| 1,679,748 A | * | 8/1928 | Stratton | 425/2 |
| 1,786,915 A | * | 12/1930 | McLean | 433/73 |
| 2,286,288 A | * | 6/1942 | Lover | 433/68 |
| 3,555,684 A | * | 1/1971 | Baum | 433/73 |
| 3,577,855 A | * | 5/1971 | Baum | 33/514 |
| 4,431,413 A | * | 2/1984 | Mack | 433/73 |
| 6,109,917 A | | 8/2000 | Lee et al. | |
| 6,209,542 B1 | * | 4/2001 | Thornton | 128/206.29 |
| 6,350,076 B1 | | 2/2002 | Wagner et al. | |
| 6,582,931 B1 | * | 6/2003 | Kois et al. | 435/56 |
| 6,884,068 B2 | * | 4/2005 | Huffman | 433/60 |
| 2003/0036032 A1 | * | 2/2003 | Jackson et al. | 433/64 |
| 2006/0121409 A1 | * | 6/2006 | Olivier | 433/73 |
| 2006/0160044 A1 | * | 7/2006 | Olivier | 433/73 |

* cited by examiner

*Primary Examiner*—Cris L Rodriguez
*Assistant Examiner*—Sunil K Singh
(74) *Attorney, Agent, or Firm*—McGarry Bair PC

(57) ABSTRACT

A device for determining the position of at least one of a dental patient's dental midline and incisal plane relative to the patient's facial midline. The device includes an impression/bite tray for obtaining a dental impression of at least one of the patient's maxillary arch and mandibular arch, and a plane indicator including at least one of a vertical alignment bar and a horizontal alignment bar, pivotally mounted to the impression/bite tray for rotatable movement relative to the impression/bite tray. The at least one of the vertical alignment bar and the horizontal alignment bar can be aligned with the dental patient's facial midline and an imaginary plane perpendicular to the facial midline, respectively, by rotating the plane indicator relative to the impression/bite tray while the impression/bite tray is retained in the patient's mouth during positioning and securing of the at least one of a vertical alignment bar and a horizontal alignment bar.

19 Claims, 9 Drawing Sheets

FACIAL PLANE INDICATOR

CROSS-REFERENCE TO RELATED APPLICATION

This application claims the benefit of U.S. provisional application Ser. No. 60/597,197, filed Nov. 16, 2005, which is incorporated herein in its entirety.

BACKGROUND OF THE INVENTION

1. Field of the Invention

The invention relates generally to dental equipment and specifically to devices for evaluating the alignment of a dental patient's dentition. In another aspect, the invention relates to a device for aligning a dental patient's dental midline and facial midline or saggital plane. In another aspect, the invention relates to a device for establishing a level horizontal incisal plane. In yet another aspect, the invention relates to an adapter for incorporating a saggital plane alignment device and/or horizontal plane indicator with a conventional impression/bite tray. In yet another aspect, the invention relates to a device for determining the pitch axis of a patient's maxillary arch.

2. Description of the Related Art

A dentist may at times be presented with the necessity of performing restorative dentistry on a patient which implicates the anterior dentition. Such dentistry may be necessary due to injury involving a loss of teeth, or the need to move teeth as a part of orthodontic treatment, or cosmetic dentistry. To ensure that an optimal patient appearance is achieved, it is typically necessary to properly align or parallel the dental midline with the facial midline, also referred to as the saggital plane, or to establish a level horizontal plane for the incisal edges. This is particularly difficult when a patient's dental midline relative to the patient's facial midline is angularly displaced.

A prior art device for indicating the dental midline relative to the facial midline and incisal plane is illustrated in FIGS. 1A and 1B. A facial plane relator 10 comprises an arch 12 terminating radially outwardly in a generally flattened arch plate 14 coplanar therewith. The medial portion of the arch plate 14 transitions into a plane indicator support 16 which is adapted to support a horizontal plane indicator 18 and a vertical plane indicator 22 in orthogonal alignment. The plane indicators 18, 22 are rod-like members. The horizontal plane indicator 18 is illustrated as permanently attached to the plane indicator support 16 coplanar with the arch plate 14, although the horizontal plane indicator 18 can alternatively be adapted for selective removal from and installation to the plane indicator support 16. The vertical plane indicator 22 is illustrated as removably attached to the plane indicator support 16 by frictional or interference engagement with a cradle 20. Extending radially inwardly from the inner edge of the arch 12 is a plurality of regularly-spaced, generally rigid fingers 24.

Referring to FIG. 1B, the facial plane relator 10 is utilized by first applying a bite registration material onto the arch 12 and support fingers 24 of the facial plane relator 10. The facial plane relator 10 is then placed into the patient's mouth. When the patient bites down on the registration material, the material extrudes toward the lips. The facial plane relator 10 can be adjusted laterally and rotationally to properly align the vertical alignment bar 22 with the patient's facial midline. After the registration material has cured, the resulting impression with the facial plane relator 10 intact is removed from the patient's mouth. This is provided to a dental lab for preparation of a dental restoration which will have a dental midline which is properly aligned with the patient's facial midline.

The prior art facial plane relator suffers from several deficiencies. First, if the volume of registration material applied to the facial plane relator is insufficient; the facial plane relator may be inadequately supported leading to inadvertent separation of the facial plane relator from the registration material. Second, alignment of the facial plane relator with the patient's facial midline requires movement of the facial plane relator, and the fingers, in a thick, high viscosity material, which can be very difficult to adjust and hold in an exact position until the material is completely set. Third, the mass of registration material must be great enough on the tray so the patient bites into the material but not on the facial plane relator. If the patient bites the facial plane relator, it will eliminate the adjustment accuracy of the facial plane relator.

SUMMARY OF THE INVENTION

An embodiment of the invention comprises a device for determining the position of either a dental patient's dental midline or incisal plane relative to the patient's facial midline. The invention includes an impression/bite tray for obtaining a dental impression of at least one of the patient's maxillary and/or mandibular arches, and a plane indicator having at least one of a vertical alignment bar and a horizontal alignment bar. The bars are pivotally mounted to the impression/bite tray for rotation, preferably through a rotatable coupling. The at least one of a vertical alignment bar and a horizontal alignment bar can be moved to alignment with the dental patient's facial midline by rotating the plane indicator relative to the impression/bite tray when the impression/bite tray is retained in the patient's mouth during positioning and securing of at least one of a vertical alignment bar and a horizontal alignment bar.

In another aspect, a device adapted for determining in combination with an impression/bite tray the position of a dental patient's dental midline or incisal plane relative to the patient's facial midline includes a plane indicator adapted for rotatable attachment to an impression/bite tray. The plane indicator includes at least one of a vertical alignment bar and a horizontal alignment bar. The at least one of a vertical alignment bar and a horizontal alignment bar are adapted to be aligned with the patient's facial midline by rotating the plane indicator relative to an impression/bite tray retained in the patient's mouth during positioning and securing of the at least one of a vertical alignment bar and a horizontal alignment bar.

In another aspect, a device for determining the position of the pitch axis of a dental patient's maxillary arch includes an impression/bite tray for obtaining a dental impression of at least one of the patient's maxillary arch and mandibular arch, and a planar alignment assembly pivotally attached to the impression/bite tray and having at least one plane alignment wing. The planar alignment assembly can be aligned with the pitch axis of the patient's maxillary arch by rotating the planar alignment assembly about a maximum of 3 orthogonal axes relative to the impression/bite tray when the impression/bite tray is retained in the patient's mouth during positioning and securing of the at least one plane alignment wing.

In yet another aspect, a method of determining the position of at least one of a dental patient's dental midline and incisal plane relative to the patient's facial midline, comprises the steps of providing an impression/bite tray with a plane indicator having at least one of a vertical alignment bar and a horizontal alignment bar rotatably mounted thereto, placing an impression material in the impression/bite tray, causing a patient to occlude at least one of the patient's maxillary and mandibular arches on the impression material, rotating the at least one of a vertical alignment bar and a horizontal alignment bar to an adjusted position in alignment with the patient's facial midline and an imaginary plane perpendicular to the facial midline, respectively, fixing the adjusted position of the at least one of a vertical alignment bar and a horizontal alignment bar relative to the impression/bite tray, and removing the impression/bite tray from the patient's mouth, whereby a dental restoration can be made from the impression that will be accurately aligned with the patient's facial midline.

DESCRIPTION OF AN EMBODIMENT OF THE INVENTION

Figures 1A, 1B:
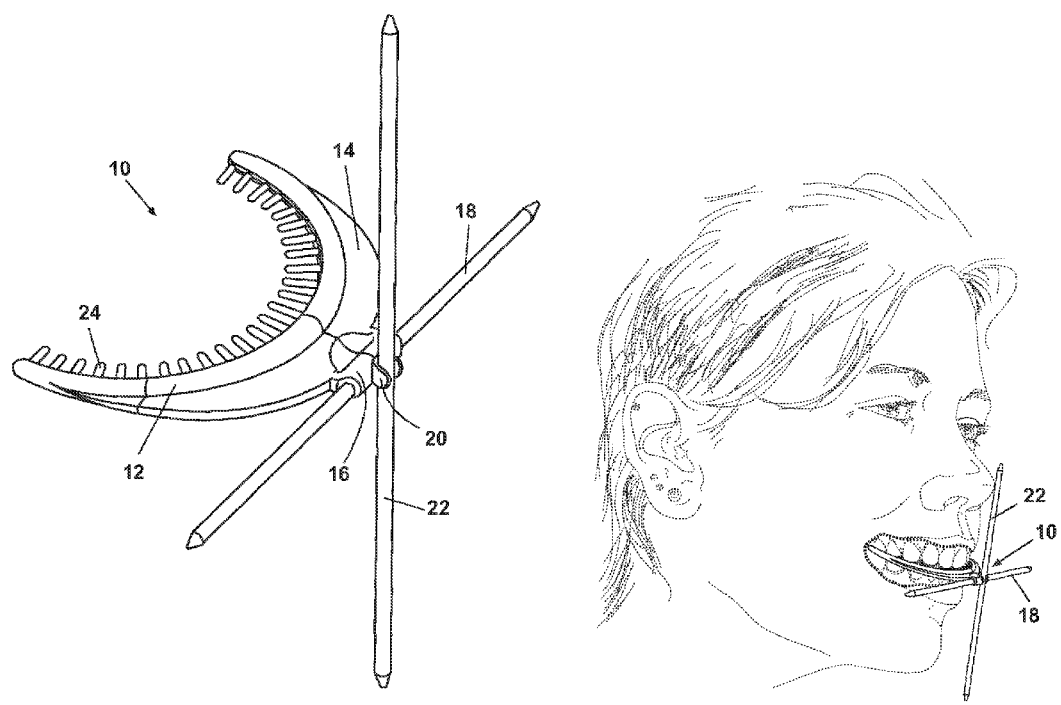
FIG. 1A is a perspective view of a prior art facial plane relator.
FIG. 1B is a perspective view of the prior art facial plane relator in position relative to a dental patient.
Figures 2A, 2B:
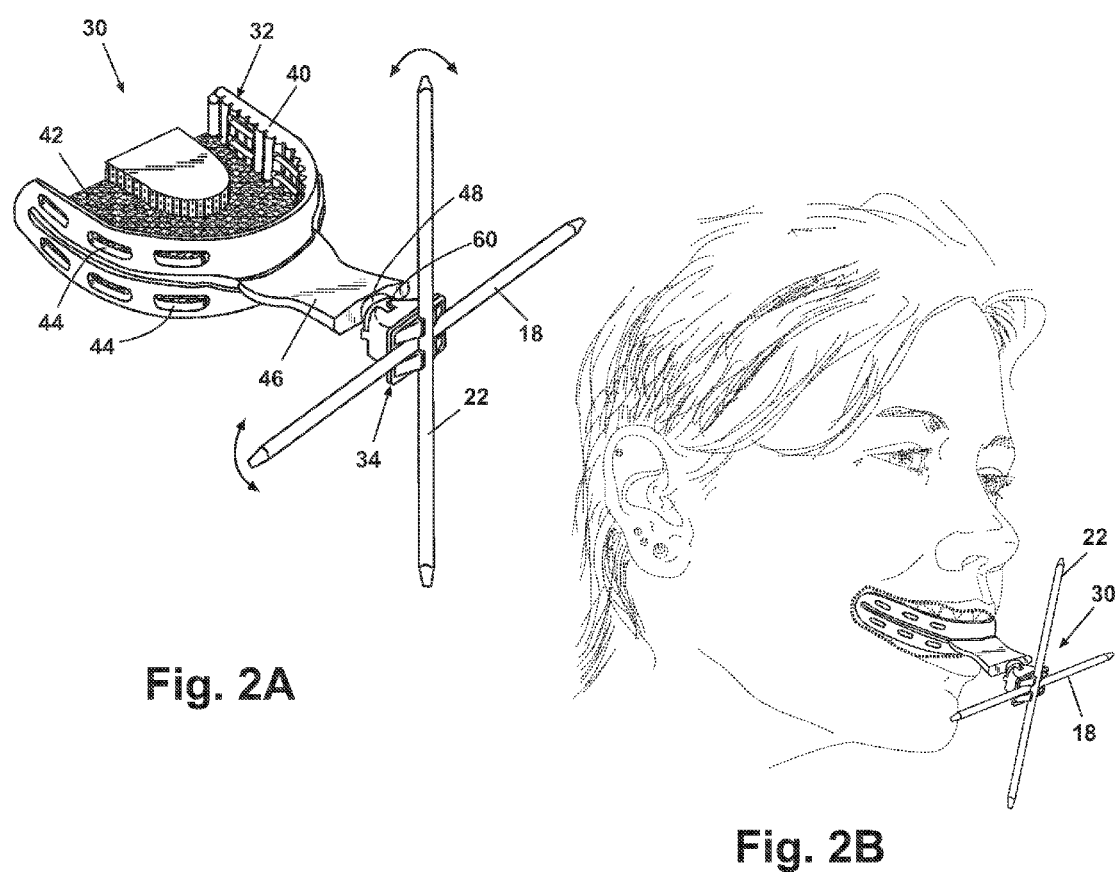
FIG. 2A is a perspective view of a facial plane indicator according to the invention.
FIG. 2B is a perspective view of the facial plane indicator illustrated in FIG. 2A in position relative to a dental patient for determining the patient's facial midline.
Figure 3A:
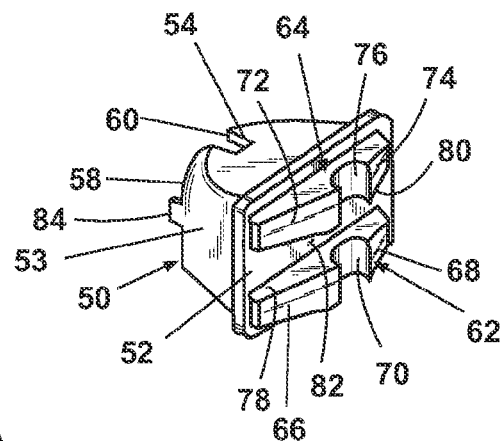
FIG. 3A is a first perspective view of a socket piece comprising a portion of the facial plane indicator of FIG. 2A.
Figure 3B:
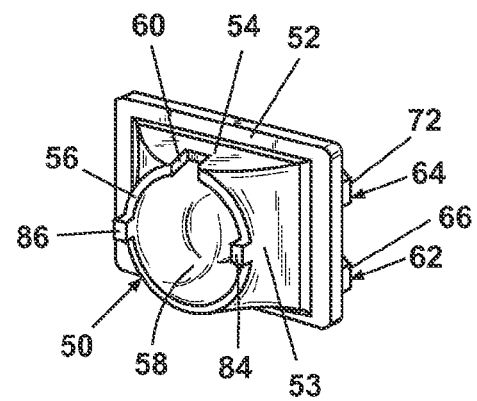
FIG. 3B is a second perspective view of the socket piece of FIG. 3A.
Figure 3C:
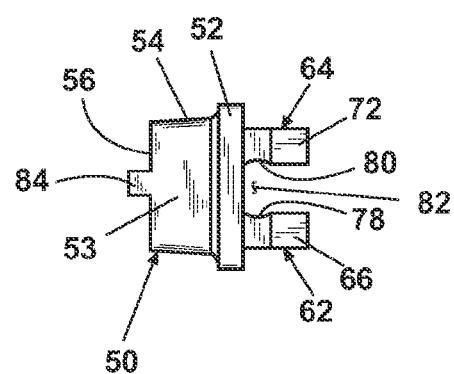
FIG. 3C is a side view of the socket piece of FIG. 3A.

Referring now to the Figures, and in particular to FIG. 2A, a facial plane indicator 30 according to the invention comprises a full arch impression/bite tray 32 and a plane indicator 34. The full arch impression/bite tray 32 is similar to a well-known impression/bite tray and comprises a curved arch wall 40 adapted for cooperative registry with a patient's upper (i.e. maxillary) and lower (i.e. mandibular) arches. It is anticipated that the impression/bite tray 32 can be adapted in different sizes to accommodate upper and lower arches having different lengths and curvatures.

The arch wall 40 is vertically bisected by a medial wall 42 to separate the impression/bite tray 32 into an upper portion and a lower portion for registry with the upper and lower arches, respectively. The impression/bite tray 32 is adapted to hold a well-known dental impression material (not shown) for producing an impression of a patient's dentition in a well-known manner, and the arch wall 40 is provided with a plurality of spaced openings 44 for extrusion of the impression material therethrough to aid in securing the impression material to the impression/bite tray 32. The openings 44 are outwardly beveled to "lock" the impression material in the impression/bite tray 32.

The anterior portion of the arch wall 40 terminates in a pedestal 46 to which is attached a rotatable coupling. The rotatable coupling is illustrated as a ball and socket-type joint comprising a ball 48 extending anteriorly of the pedestal 46. The pedestal 46 has dimensions sufficient for the rigid attachment of the ball 48 to the arch wall 40, and to locate the plane indicator 34 anteriorly of the patient's nose and chin. The pedestal also serves as a grip for the dentist to use to facilitate the insertion, positioning, and removal of the impression/bite tray 32. The ball 48 is aligned with the arch wall 40 so that the centerline of the ball 48 is coextensive with a vertical medial plane of the arch wall 40.

Referring also to FIGS. 3A-C and 4, the plane indicator 34 comprises a socket piece 50, a horizontal alignment bar 90, and a vertical alignment bar 92. The socket piece 50 comprises part of the ball and socket-type joint, and has a center wall 52 and a somewhat D-shaped socket body 53 having an upper wall 54 extending orthogonally from the center wall 52. Centered within the socket body 53 is a semi-spherical socket 58 adapted for cooperative registry with the ball 48 and circumscribed by a rim 56. The socket 58 is configured to enclose and retain the ball 48 therein, and to enable the ball 48 to rotate freely with slight friction. Extending longitudinally away from the rim 56 are a pair of diametrically-opposed, parallel fingers 84, 86 adapted to facilitate retention of the ball 48 in the socket 58 by "gripping" the ball 48 in the socket 58. Extending inwardly from the rim 56 through an upper portion of the circumferential wall 54 is a slot 60. The precise configuration of the ball 48 and socket 58 can be adapted to provide a selected degree of yaw, pitch, and roll of the plane indicator 34 relative to the impression/bite tray 32. While a particular configuration of the socket body 53 has been described, alternate configurations of the socket body 53 can be used which are suitable for cooperative registry with the ball 48 to provide the functionality described herein.

Extending from the center wall 52 opposite the socket 58 is a lower yoke 62 and an upper yoke 64 for supporting the horizontal alignment bar 90 and the vertical alignment bar 92. The lower yoke 62 comprises a pair of wedge-shaped buttresses 66, 68 separated by a curved lower cradle 70 adapted for frictional or interference attachment of the vertical alignment bar 92. The upper yoke 64 comprises a pair of wedge-shaped buttresses 72, 74 separated by a curved upper cradle 76 adapted for frictional or interference attachment of the vertical alignment bar 92. The lower yoke 62 and the upper yoke 64 are adapted so that the lower cradle 70 and the upper cradle 76 are coaxially aligned.

The lower yoke 62 has an upper surface 78, and the upper yoke 64 has a lower surface 80 defining a slot 82 extending orthogonal to the centerline of the lower cradle 70 and the upper cradle 76. The upper surface 78 and the lower surface 80 are curved about the longitudinal axis of the slot 82 for frictional or interference attachment of the horizontal alignment bar 90.

The plane indicator 34 is assembled to the impression/bite tray 32 by inserting the ball 48 in the socket 58. The socket 58 is adapted so that the ball 48 is snapfit therein but with sufficient play to enable the ball 48 to rotate freely in the socket 58 with slight friction. The fingers 84, 86 facilitate the retention of the ball 48 in the socket 58. The slot 60 extends through the socket wall to the ball 48.

The horizontal alignment bar 90 can then be seated in the slot 82 followed by seating of the vertical alignment bar 92 into the lower cradle 70 and the upper cradle 76. It will be recognized that the cradles 70, 76 are spaced away from the center wall 52 a distance approximately equal to the diameter of the horizontal alignment bar 90 to ensure that the vertical alignment bar 92 clears the horizontal alignment bar 90. Alternatively, the vertical alignment bar 92 can be provided with a curved cut out adapted for registry with the horizontal alignment bar 90 when the alignment bars 90, 92 are assembled in the plane indicator 34.

The facial plane indicator 30 is used by first applying a sufficient quantity of impression material to the impression/bite tray 32 in a well-known manner and positioning the impression/bite tray 32 in the patient's mouth so that the ball 48 lines up with the patient's facial midline and the patient can bite down on the impression/bite tray 32. The dentist then completes the well-known impression technique. After the impression material is fully set, while the impression/bite tray 32 is still fully seated in the patient's mouth, the plane indicator 34 is assembled to the impression/bite tray 32 as described above. The plane indicator 34 can then be rotated so that the vertical alignment bar 92 is aligned with the patient's facial midline. A small quantity of adhesive can be applied to the slot 60 to fix the ball 48 in the socket 58. After the adhesive is cured (normally in very short time), the facial plane indicator 30 can be removed from the patient's mouth, even before the impression material is fully cured. The alignment bars 90, 92 can be removed from the plane indicator 34 to facilitate packaging and transportation of the facial plane indicator 30 to a dental laboratory.

Figure 5A:
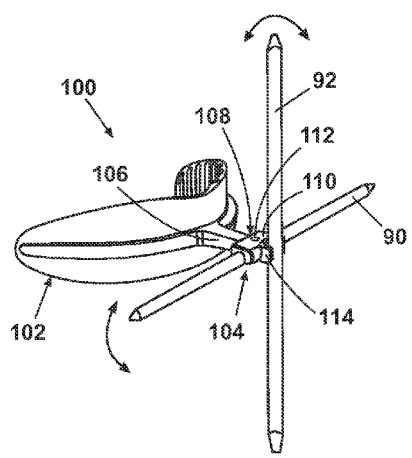
FIG. 5A is a perspective view of a second embodiment of a facial plane indicator according to the invention.
Figure 5B:
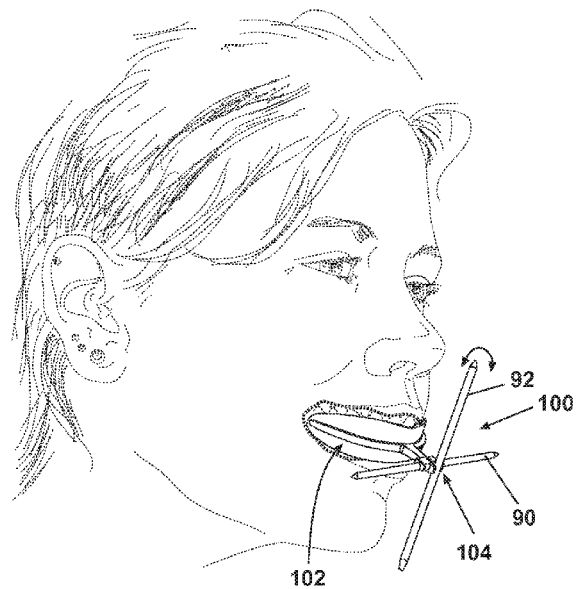
FIG. 5B is a perspective view of the facial plane indicator illustrated in FIG. 5A in position relative to a dental patient for determining the patient's facial midline.

Referring now to FIGS. 5A and B, an alternative facial plane indicator 100 is illustrated. The facial plane indicator 100 comprises an impression/bite anterior quadrant tray 102 and a plane indicator 104. The impression/bite tray 102 is illustrated as an anterior tray rather than a full arch tray as illustrated in FIG. 2A. The facial plane indicator 30 illustrated in FIG. 2A can incorporate an anterior tray. Similarly, the facial plane indicator 100 can incorporate a full arch impression/bite tray.

The plane indicator 104 comprises a pedestal 106 extending longitudinally away from the anterior portion of the impression/bite tray 102, and terminating in a rotatable coupling comprising a plane indicator support 108. The plane indicator support 108 comprises a generally rectilinear, block like rotating block 110 having an aperture 112 extending into the interior of the block 110. Extending laterally through the block 110 is a horizontal alignment bar 90. The horizontal alignment bar 90 can be integrally formed with the block 110 or can be snapfit to the block 110 through a suitable connection incorporated into the block 110. Extending longitudinally away from the block 110 is a cradle 114 adapted to retain a vertical alignment bar 92 in a position orthogonal to the horizontal alignment bar 90.

Figure 6:
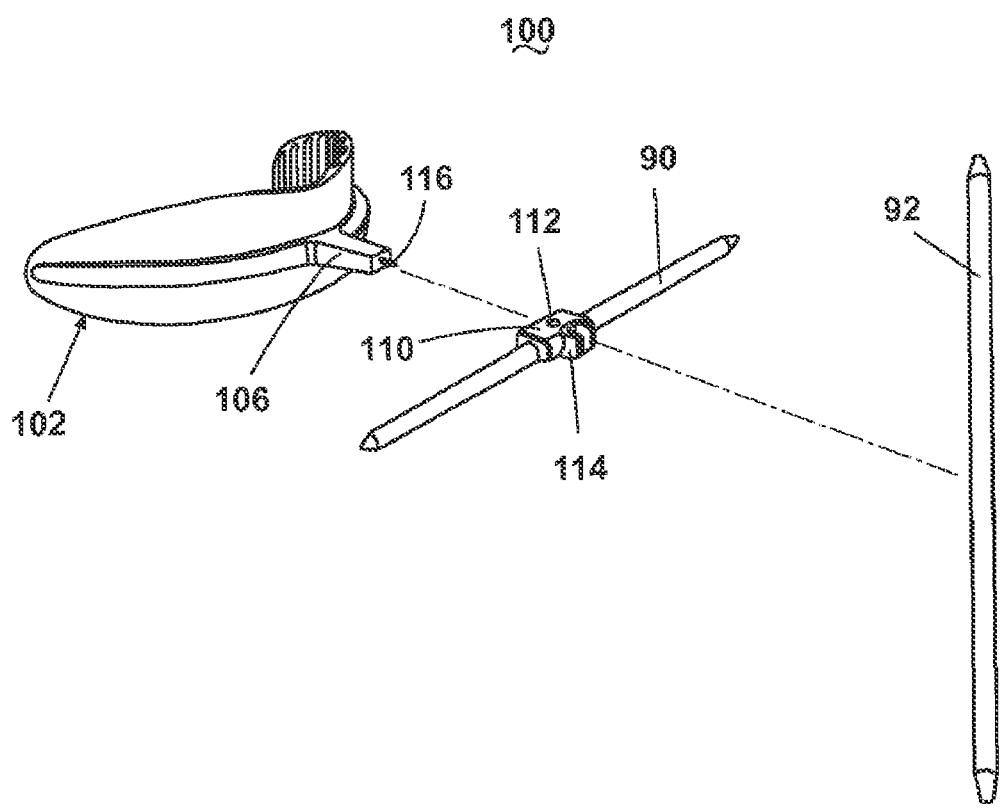
FIG. 6 is an exploded view of the facial plane indicator illustrated in FIG. 5A.

Referring also to FIG. 6, a pin-like shaft 116 extends longitudinally from the pedestal 106 for registry with a bore (not shown) in the block 110. The bore is in fluid communication with the aperture 112.

The facial plane indicator 100 is utilized to determine a patient's facial midline in a similar manner as previously described with respect to the facial plane indicator 30. Rather than rotating through a ball and socket connection, the plane indicator 104 is rotated about the shaft 116 until the vertical alignment bar 92 is suitably aligned with a patient's facial midline. An adhesive is then applied through the aperture 112 to fix the block 110 on the shaft 116 so the facial plane indicator 100 can be removed from the patient's mouth without waiting for the impression material to cure. The facial plane indicator 100, with the impression of the patient's dentition, can then be packaged and submitted to a dental laboratory. The vertical alignment bar 92 can be readily removed from the plane indicator 104 to facilitate packaging and transportation to the laboratory.

Figure 7:
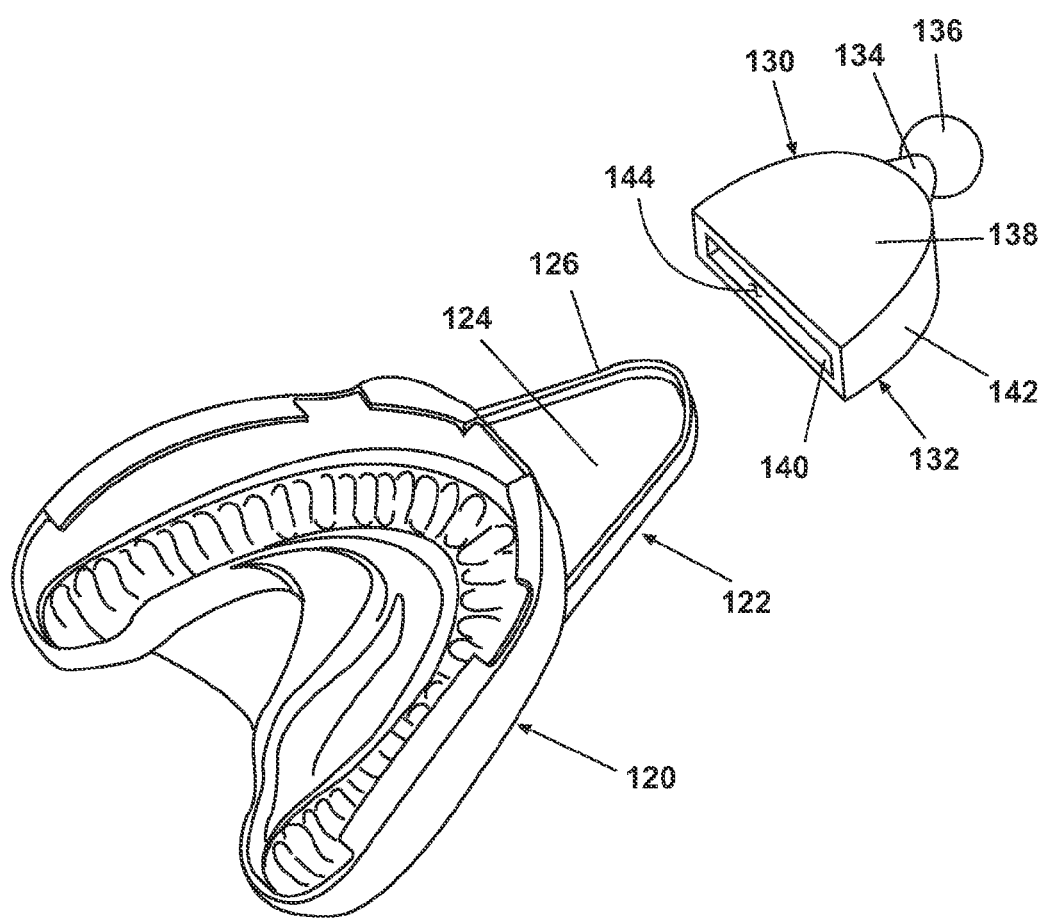
FIG. 7 is a perspective view of a third embodiment of a facial plane indicator according to the invention.

FIG. 7 illustrates an embodiment of a facial plane indicator which can be utilized with a conventional impression/bite tray 120. The impression/bite tray 120 is illustrated as comprising a grip plate 122 having an inner web 124 bordered by a raised lip 126, although impression/bite trays with differently configured handles can be used.

A ball adapter 130 comprises a somewhat D-shaped sleeve 132 transitioning through a pedestal 134 to a ball 136. The sleeve 132 is a somewhat flattened hollow body comprising a D-shaped top wall 138 in parallel spaced disposition from a bottom wall 140. A curved wall 142 extends between the top wall 138 and the bottom wall 140 to define a grip plate cavity 144 therebetween. The cavity 144 is adapted for slidable receipt of the grip plate 122. The pedestal 134 extends longitudinally away from the anterior portion of the curved wall 142. The ball 136, in a manner similar to the ball 48, is adapted for rotational registry with the socket 58 of the plane indicator 34 to comprise the rotatable coupling. With the ball adapter 130 attached to the impression/bite tray 120, and the plane indicator 34 attached to the ball 136, a dental patient's facial midline can be determined by manipulation of the plane indicator 34 as previously described.

Figure 8:
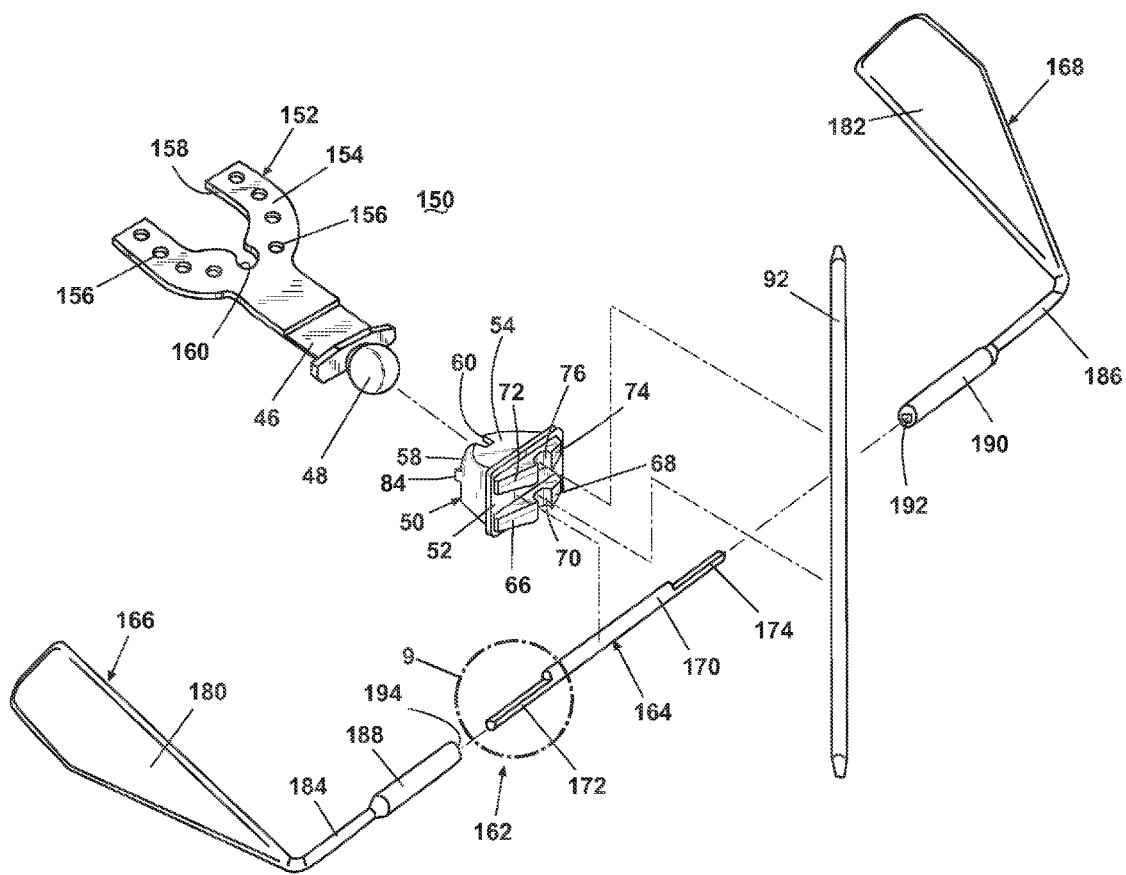
FIG. 8 is an exploded view of a fourth embodiment of a facial plane indicator according to the invention.

FIG. 8 illustrates an embodiment of the facial plane indicator 150 that shares many elements of the previously described facial plane indicator 30. Thus, like elements are identified with like numbering.

The facial plane indicator 150 comprises a generally planar, arch-shaped impression/bite plate 152 having a bite wall 154 with a plurality of extrusion apertures 156 extending therethrough. The impression/bite plate 152 is adapted to carry a dental impression material for obtaining an impression of a patient's maxillary arch in a generally well-known manner. The arms of the impression/bite plate 152 define a medial opening 158 extending medially therebetween, terminating anteriorly at the apex of the impression/bite plate 152 in an incisal papilla pin opening 160 to enable the use of an incisal papilla pin (not shown) with an occlusal analyzer articulator for reconstructive workups.

Figure 9:
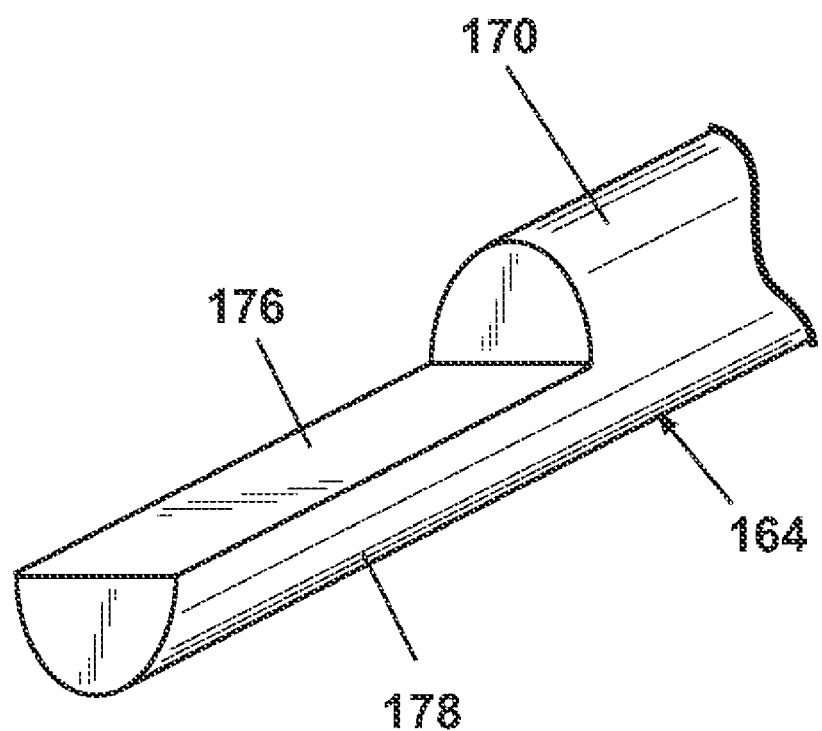
FIG. 9 is an enlarged view of a portion of the facial plane indicator illustrated in FIG. 8.

Extending away from the apex of the impression/bite plate 152 is a pedestal 46 terminating in a ball 48. A socket piece 50 is rotatably attached to the ball 48 and adapted for attachment of a vertical alignment bar 92 as previously described. A horizontal/planar alignment assembly 162 comprises a horizontal alignment bar 164 and a pair of opposed planar alignment wings 166, 168. The horizontal alignment bar 164 comprises an elongated, rod-like shaft 170 transitioning to a pair of longitudinally-aligned, opposed lateral shafts 172, 174. As illustrated in FIG. 9, the lateral shafts 172, 174 have a notch 176 defining a semi-cylindrical keyed end 178. The shaft 170 can be received between the buttresses 72, 74 as previously described.

The plane alignment wing 166, 168 comprises a wing portion 180, 182 attached to and aligned generally orthogonally to a support shaft 184, 186. The support shaft 184, 186 comprises a key portion 188, 190 having a semi-cylindrical channelway 192, 194 extending therein and adapted for slidable receipt of the semi-cylindrical keyed end 178 therein. With the semi-cylindrical keyed end 178 inserted into the channelway 192, 194, the plane alignment wing 166, 168 will extend generally orthogonally to the axis of the horizontal alignment bar 164 and can be positioned laterally adjacent to the patient's maxilla and mandible when the horizontal alignment bar 164 is received between the buttresses 72, 74. The plane alignment wing 166, 168 can then be rotated about the medial shaft 170 for alignment with the pitch axis of the maxillary arch. Additional alignment positions can be obtained through manipulation of the facial plane indicator 150 through the rotatable coupling as previously described. The horizontal alignment bar 164 is maintained in its selected alignment position through the use of a suitable adhesive or a friction fit. Alternatively, the buttresses 72, 74 can be adapted for frictionally supporting the vertical alignment bar 164.

The lateral shaft 172, 174, and the semi-cylindrical channelway 192, 194 can be configured using other than a semi-cylindrical section, such as a square, an octagon, and the like. After removal of the facial plane indicator 150 from the patient's mouth, the plane alignment wings 166, 168 can be removed from the horizontal alignment bar 164 to facilitate transportation of the facial plane indicator to a laboratory. At the laboratory, the plane alignment wings 166, 168 can be reattached to the horizontal alignment bar 164 to define the pitch axis of the maxillary arch.

Figure 4:
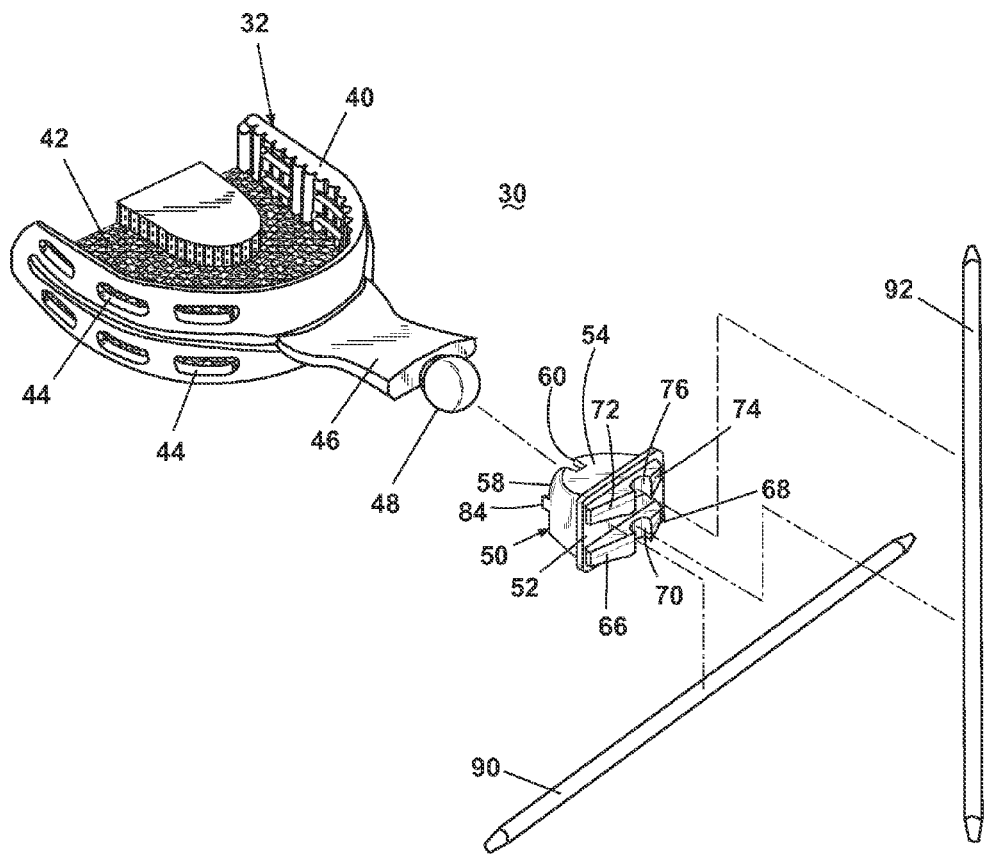
FIG. 4 is an exploded view of the facial plane indicator illustrated in FIG. 2A.

Alternatively, the facial plane indicator 150 can comprise a full arch impression/bite tray configured as illustrated in FIGS. 2A and 4. The vertical/planar alignment assembly 162 can also be configured with the socket piece 50 and the vertical alignment bar 92 for registry with a ball adapter 130 and an impression/bite tray 120 as illustrated in FIG. 7.

The facial plane indicator described herein provides a convenient and accurate means of determining a patient's facial midline in order to align a patient's facial midline and dental midline through restorative or cosmetic dentistry. The use of a well-known impression/bite tray facilitates the dentist's use of the inventive facial plane indicator, which insures an accurate alignment. The ball and socket type connection eliminates the need to manipulate the entire device, and limits the movable parts to the alignment bars, thereby enhancing ease of use and accuracy. The alignment bars can be readily removed to facilitate packaging and transport of the facial plane indicator to a dental laboratory.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

What is claimed is:

1. A facial plane indicator for determining the position of at least one of a dental patient's dental midline and incisal plane relative to the patient's facial midline, comprising:
    an impression/bite tray fixedly coupled with a first end of an anteriorly-disposed rigid pedestal;
    a first constituent part, comprising a first side and a second side, of a rotatable joint assembly including a semi-spherical concavity disposed on the first side with at least one of a horizontally-disposed arcuate cradle and a vertically-disposed arcuate cradle disposed on the second side, the at least one arcuate cradle being defined by at least one wedge-shaped buttress;
    at least one of a horizontal alignment rod and a vertical alignment rod adapted for seating in the at least one of a horizontally-disposed arcuate cradle and a vertically-disposed arcuate cradle, respectively; and
    a second constituent part of a rotatable joint assembly including a sphere coupled with a second end of the rigid pedestal; and wherein the sphere is adapted to be coupled with said semi-spherical concavity;
    wherein the at least one of a horizontal alignment rod and a vertical alignment rod can be seated in the at least one of a horizontally-disposed arcuate cradle and a vertically-disposed arcuate cradle, respectively, and aligned with an orientation of a dental patient's incisal plane, facial midline and an imaginary plane perpendicular to the facial midline, and a plane parallel to the facial midline and orthogonal to the imaginary plane, by rotating the first constituent part of a rotatable joint assembly about a maximum of 3 orthogonal axes relative to the second constituent part of a rotatable joint assembly while the impression/bite tray is occlusally retained in a patient's mouth.

2. The facial plane indicator according to claim 1 wherein the second constituent part is mounted to the second end of the rigid pedestal by a selectively removable adapter.

3. The facial plane indicator according to claim 2, further comprising an opening associated with the sphere and the semi-spherical concavity.

4. The facial plane indicator according to claim 3 wherein the first constituent part can be selectively immobilized relative to the second constituent part by applying an adhesive to the sphere and the semi-spherical concavity through the opening.

5. The facial plane indicator according to claim 1 wherein the horizontal alignment rod terminates in no more than two opposed alignment wings with planar wing portions for determining the pitch axis of a patient's maxillary arch.

6. The facial plane indicator according to claim 5 wherein the no more than two opposed alignment wings are removably attached to the horizontal alignment rod.

7. The facial plane indicator according to claim 1 wherein the at least one of a horizontal alignment rod and a vertical alignment rod is selectively detachable from the at least one of a horizontally-disposed arcuate cradle and a vertically-disposed arcuate cradle, respectively.

8. A device adapted for determining, in combination with an impression/bite tray fixedly coupled with a first end of an anteriorly-disposed rigid pedestal, the position of at least one of a dental patient's dental midline and incisal plane relative to the patient's facial midline, comprising:
    a first constituent part, comprising a first side and a second side, of a rotatable joint assembly including a semi-spherical concavity disposed on the first side with at least one of a horizontally-disposed arcuate cradle and a vertically-disposed arcuate cradle disposed on the second side, the at least one arcuate cradle being defined by at least one wedge-shaped buttress;
    at least one of a horizontal alignment rod and a vertical alignment rod selectively attachable to the at least one of a horizontally-disposed arcuate cradle and a vertically-disposed arcuate cradle, respectively; and
    a second constituent part of a rotatable joint assembly including a sphere and adapted for coupling with a second end of a rigid pedestal;
    wherein the semi-spherical concavity can be snapfit with the sphere for relative rotation of the sphere and the semi-spherical concavity, and retention of the sphere therein; and
    wherein the at least one of a horizontal alignment rod and a vertical alignment rod can be rotated about a maximum of 3 orthogonal axes by relative rotation of the sphere and the semi-spherical concavity, and aligned with an orientation of a dental patient's incisal plane, facial midline and an imaginary plane perpendicular to the facial midline, and a plane parallel to the facial midline and orthogonal to the imaginary plane.

9. The device according to claim 8, further comprising an adapter for selectively attaching the second constituent part to a second end of a rigid pedestal.

10. The device according to claim 9, further comprising an opening associated with the sphere and the semi-spherical concavity.

11. The device according to claim 10 wherein the first constituent part can be selectively immobilized relative to the second constituent part by applying an adhesive to the sphere and the semi-spherical concavity through the opening.

12. The device according to claim 8 wherein the horizontal alignment rod terminates in no more than two opposed alignment wings with planar wing portions that can be oriented for coplanar alignment with a patient's occlusal plane.

13. The device according to claim 12 wherein the no more than two opposed alignment wings are removably attached to the horizontal alignment rod.

14. A facial plane indicator for determining the orientation of the pitch axis of a dental patient's maxillary arch, comprising:

an impression/bite tray fixedly coupled with a first end of an anteriorly-disposed rigid pedestal;

a first constituent part, comprising a first side and a second side of a rotatable joint assembly including a semi-spherical concavity disposed on the first side with at least one of a horizontally-disposed arcuate cradle and a vertically-disposed arcuate cradle disposed on the second side, the at least one arcuate cradle being defined by at least one wedge-shaped buttress;

at least one of a horizontal alignment rod terminating in no more than two opposed alignment wings with planar wing portions and a vertical alignment rod, adapted for seating in the at least one of a horizontally-disposed arcuate cradle and a vertically-disposed arcuate cradle, respectively; and a second constituent part of a rotatable joint assembly including a sphere coupled with a second end of the rigid pedestal;

and wherein the sphere is adapted to be coupled with said semi-spherical concavity;

wherein the first constituent part can be aligned with the pitch axis of a patient's maxillary arch, while the impression/bite tray is occlusally retained in the patient's mouth, by relative rotation of the sphere and the semi-spherical concavity about a maximum of 3 orthogonal axes and aligning the no more than two opposed alignment wings coplanar with the pitch axis of the patient's maxillary arch.

15. The facial plane indicator according to claim 14, further comprising an adapter for selectively attaching the second constituent part to the second end of the rigid pedestal.

16. The facial plane indicator according to claim 15, further comprising an opening associated with the sphere and the semi-spherical concavity.

17. The facial plane indicator according to claim 16 wherein the first constituent part can be selectively immobilized relative to the second constituent part by applying an adhesive to the sphere and the semi-spherical concavity through the opening.

18. The facial plane indicator according to claim 14 wherein the no more than two opposed alignment wings are removably attached to the horizontal alignment rod.

19. A method of determining the position of at least one of a dental patient's dental midline and incisal plane relative to the patient's facial midline, comprising the steps of:

providing an impression/bite tray fixedly coupled with a first end of an anteriorly-disposed rigid pedestal;

providing a first constituent part, comprising a first side and a second side, of a rotatable joint assembly including a semi-spherical concavity disposed on the first side with at least one of a horizontally-disposed arcuate cradle and a vertically-disposed arcuate cradle disposed on the second side, the at least one arcuate cradle being defined by at least one wedge-shaped buttress;

seating the at least one of a horizontal alignment rod and a vertical alignment rod in the at least one of a horizontally-disposed arcuate cradle and a vertically-disposed arcuate cradle, respectively;

coupling the first constituent part with a second constituent part of a rotatable joint assembly including a sphere coupled with a second end of the rigid pedestal, the coupling effected by seating the sphere in the semi-spherical concavity;

placing an impression material in the impression/bite tray;

causing a patient to occlude at least one of the patient's maxillary and mandibular arches in the impression material to provide an impression of at least one of the patient's maxillary and mandibular arches;

rotating the at least one of the vertical alignment rod and the horizontal alignment rod about a maximum of 3 orthogonal axes to an adjusted position in alignment with the patient's facial midline and an imaginary plane perpendicular to the facial midline, respectively, and a plane parallel to the facial midline and orthogonal to the imaginary plane;

affixing the sphere in the semi-spherical concavity in the adjusted position to prevent relative movement therebetween; and removing the impression/bite tray from the patient's mouth;

whereby a dental restoration can be made from the impression that will be accurately aligned with at least one of the patient's facial midline and incisal plane.

* * * * *